(12) United States Patent
Jacobs

(10) Patent No.: US 7,534,216 B2
(45) Date of Patent: May 19, 2009

(54) CORRECTIVE ORTHESIS

(76) Inventor: Klaus-Jürgen Jacobs, Karlstrasse 14, 64546 Mörfelden-Walldorf (DE)

( * ) Notice: Subject to any disclaimer, the term of this patent is extended or adjusted under 35 U.S.C. 154(b) by 620 days.

(21) Appl. No.: 10/490,661

(22) PCT Filed: Oct. 16, 2002

(86) PCT No.: PCT/EP02/11566

§ 371 (c)(1), (2), (4) Date: Sep. 7, 2004

(87) PCT Pub. No.: WO03/032873

PCT Pub. Date: Apr. 24, 2003

(65) Prior Publication Data

US 2005/0033208 A1 Feb. 10, 2005

(30) Foreign Application Priority Data

Oct. 17, 2001 (DE) ................................ 201 17 080

(51) Int. Cl.
*A61F 13/00* (2006.01)
(52) U.S. Cl. ................................ 602/16; 602/5; 602/20
(58) Field of Classification Search ................ 602/5–8, 602/16, 20, 23, 26, 27
See application file for complete search history.

(56) References Cited

U.S. PATENT DOCUMENTS

| 3,976,057 | A |   | 8/1976  | Barclay |             |
|-----------|---|---|---------|---------|-------------|
| 5,144,943 | A |   | 9/1992  | Luttrell et al. | |
| 5,285,773 | A |   | 2/1994  | Bonutti et al. | |
| 5,462,518 | A |   | 10/1995 | Hatley et al. | |
| 5,653,680 | A |   | 8/1997  | Cruz    |             |
| 5,662,693 | A |   | 9/1997  | Johnson et al. | |
| 5,891,061 | A | * | 4/1999  | Kaiser  | ......... 601/33 |
| 6,478,758 | B1 | * | 11/2002 | Hassler | ............ 602/5 |
| 2003/0093018 | A1 | * | 5/2003 | Albrecht et al. | ........ 602/16 |

FOREIGN PATENT DOCUMENTS

| EP | 0 564 734  | 10/1993 |
| EP | 1 138 286  | 10/2001 |
| EP | 1 306 065  | 5/2003  |
| WO | WO 00/09066 | 2/2000 |

\* cited by examiner

*Primary Examiner*—Kim M Lewis
(74) *Attorney, Agent, or Firm*—McGlew and Tuttle, P.C.

(57) ABSTRACT

The Quengle cast (1) has an adjusting member for generating a Quengle force acting on the joint. The adjusting member is part of a correcting unit with a pressurized basic body. To generate a defined Quengle force, a pressure that can be preset by means of a control unit (5) can be set in the basic body, as a result of which the adjusting member can be deflected in relation to the basic body.

45 Claims, 7 Drawing Sheets

CORRECTIVE ORTHESIS

FIELD OF THE INVENTION

The present invention pertains to a Quengle/Quengel type hinged cast/splint for the correction of false positions of joints with an adjusting member for generating a Quengle/corrective force acting on the joint.

BACKGROUND OF THE INVENTION

Such Quengle casts or Quengle splints are used in the areas of surgery or orthopedics to correct stiffened human joints or false positions of human extremities. The Quengle cast extends over the joint, and is arranged at the particular extremities such that the restriction of the movement of the joint, fixed in a pathological bent or extended position, is corrected. The Quengle cast typically has for this purpose two cast parts, which can be pivoted in relation to each other and are moved in relation to each other by means of a mechanical Quengle traction mechanism or Quengle pressure, as a result of which the joint of the extremity located in the Quengle cast is brought closer to the particular normal position.

The mechanical Quengle traction mechanisms operate with tension and compression springs, elastic traction mechanisms, toothed spindle hinges, cables or the like, which act on levers of the Quengle cast.

The drawback of such systems is that reproducible and controllable setting of the Quengle forces that act on the joint is not possible in such systems.

It is disadvantageous, in particular, that it is therefore impossible to check the therapeutic result in the course of the treatment of the joint.

It is particularly disadvantageous here that the adaptation of the Quengle forces is possible only inaccurately as the correction progresses.

SUMMARY OF THE INVENTION

A basic object of the present invention is to design a Quengle cast of the type described in the introduction such that controlled therapy of stiffening and false positions of anatomic joints becomes possible.

The Quengle cast according to the present invention for correcting false positions of joints has an adjusting member for generating a Quengle force acting on the joint. The adjusting member is part of a correcting unit with a pressurized basic body. To generate a defined Quengle force, a pressure that can be preset by means of a control unit can be set in the basic body, as a result of which the adjusting member can be deflected in relation to the basic body.

Thus, the basic idea of the present invention is to use a pressure control system or pressure regulation system controlled via a control unit instead of mechanical systems in order to preset the Quengle forces. The deflection of the adjusting member brought about by the pressure and the Quengle force of the Quengle cast, which is exerted as a result, can thus also be preset exactly and reproducibly. The Quengle forces are also preset accurately over longer periods of time corresponding to the preset values that can be selected by the user, and, moreover, the presetting can be checked on the control unit by means of corresponding displays. As a result, complete and accurate therapy control is guaranteed during the entire duration of the therapy.

In an especially advantageous embodiment of the present invention, the correcting unit is designed as a pneumatic correcting unit. The basic body is now designed in the form of a hollow cylinder, in which the rear part of a piston rod forming the adjusting member is mounted displaceably in the longitudinal direction of the hollow cylinder. The displacement of the piston rod for generating the Quengle force takes place by means of a bellows, which is supplied by the control unit with compressed air. An air reservoir, through which compressed air is sent into the bellows of the hollow cylinder by means of a pump via a flexible tube connection, is provided for this purpose in the control unit. The control unit has, moreover, a computer unit, which assumes especially the actuation of the pump.

It is possible to preset the pressure in the hollow cylinder with an especially good accuracy with this pneumatic pressure regulating system with little design effort, and the Quengle forces can thus be set accurately. It proved to be expedient to operate with a low air pressure in the hollow cylinder to generate the Quengle forces. The air pressure in the bellows of the hollow cylinder is especially advantageously in the range between 0.4 cm/Hg and 250 cm/Hg.

To make placement possible on the particular body, the volume in the interior of the bellows is considerably smaller than the volume of the air reservoir in the control unit. It is thus possible to rapidly compensate for rapid pressure changes in the bellows, which occur during the treatment and may be caused by sudden movements of the joint. This happens especially when Quengle casts are used to correct contractures caused by spasm. When spasm develops, the sudden movement of the joint exerts an impulse on the piston rod, so that the piston rod is pushed into the hollow cylinder. The pressure increase caused by this in the interior of the bellows is rapidly compensated by the coupling with the bulky air reservoir. This property of the Quengle cast according to the present invention is an essential prerequisite for the ability to affect flexion contractures with this cast in patients with spasm.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
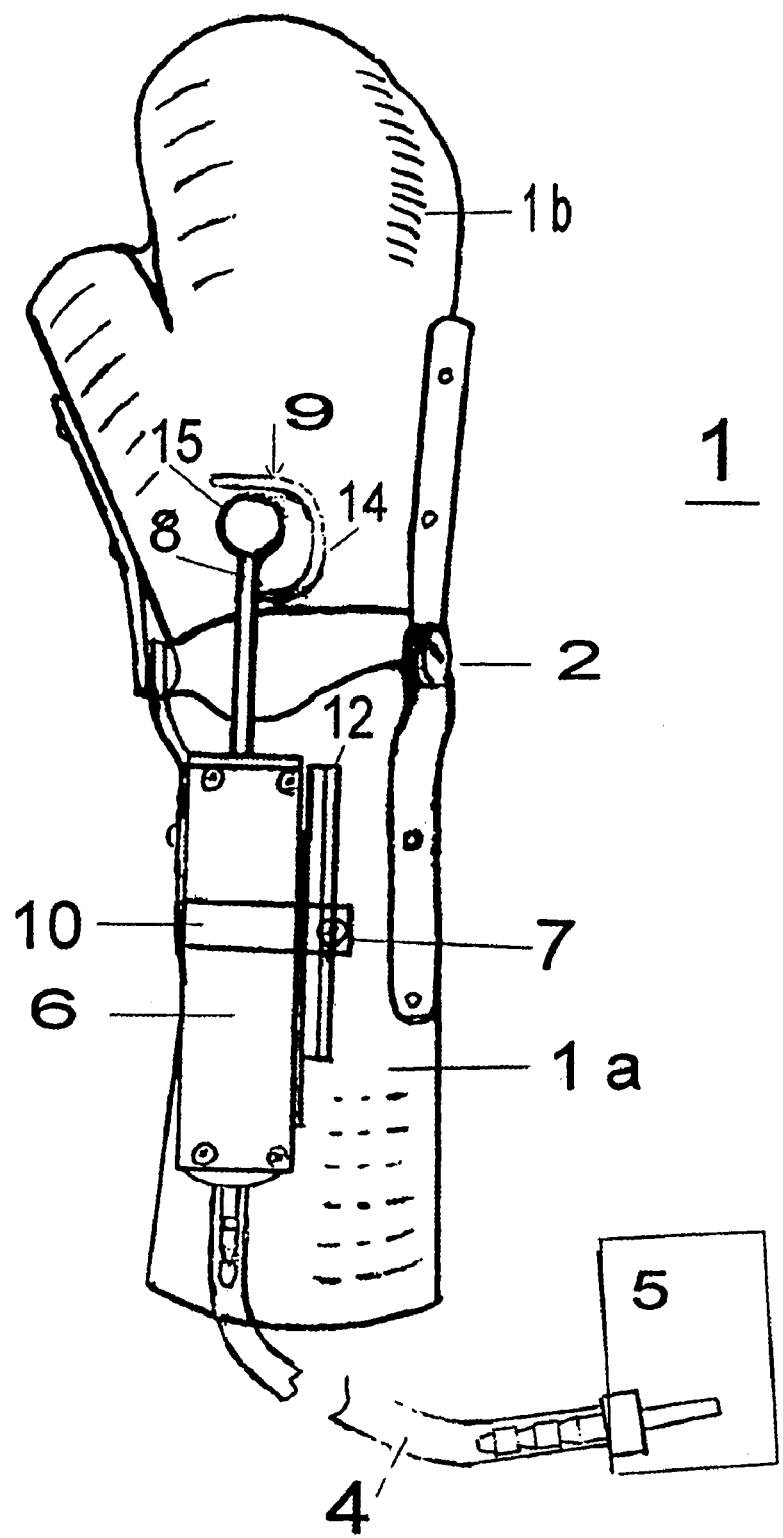
FIG. 1 is a top view of the palm side of a Quengle hand cast designed as a hand cast.
Figure 2:
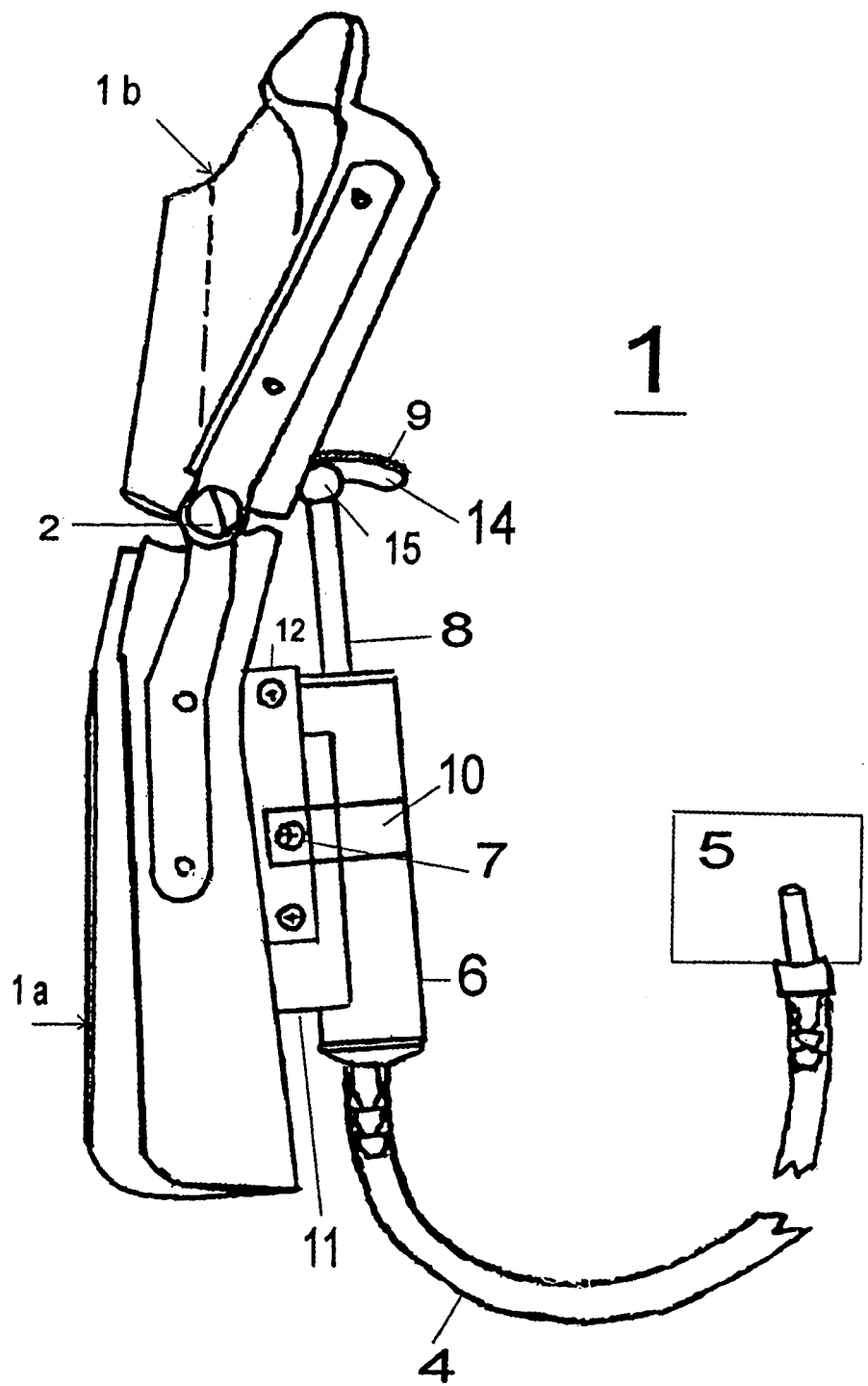
FIG. 2 is a side view of the hand cast according to FIG. 1.

Referring to the drawings in particular, FIGS. 1 and 2 show a first exemplary embodiment of the Quengle cast 1 according to the present invention. The Quengle cast 1 is designed as a hand cast in this case and is used for the therapy of stiffening or false positions of human hand joints.

The hand cast comprises essentially a first cast part 1a and a second cast part 1b, which are connected to each other in an articulated manner. The first cast part 1a is used to support a lower arm, and the second cast part 1b is used to support the hand connected to it.

A correcting unit, which is designed as a pneumatic correcting unit 3 in this case, is fastened to the hand cast. It is also possible, in principle, to use hydraulic correcting units or the like. The pneumatic correcting unit 3 is connected to a control unit 5 via a flexible tube 4.

The pneumatic correcting unit 3 controlled via the control unit 5 is used to preset a Quengle force, with which the hand joint is forced in a preset direction.

Figure 3:
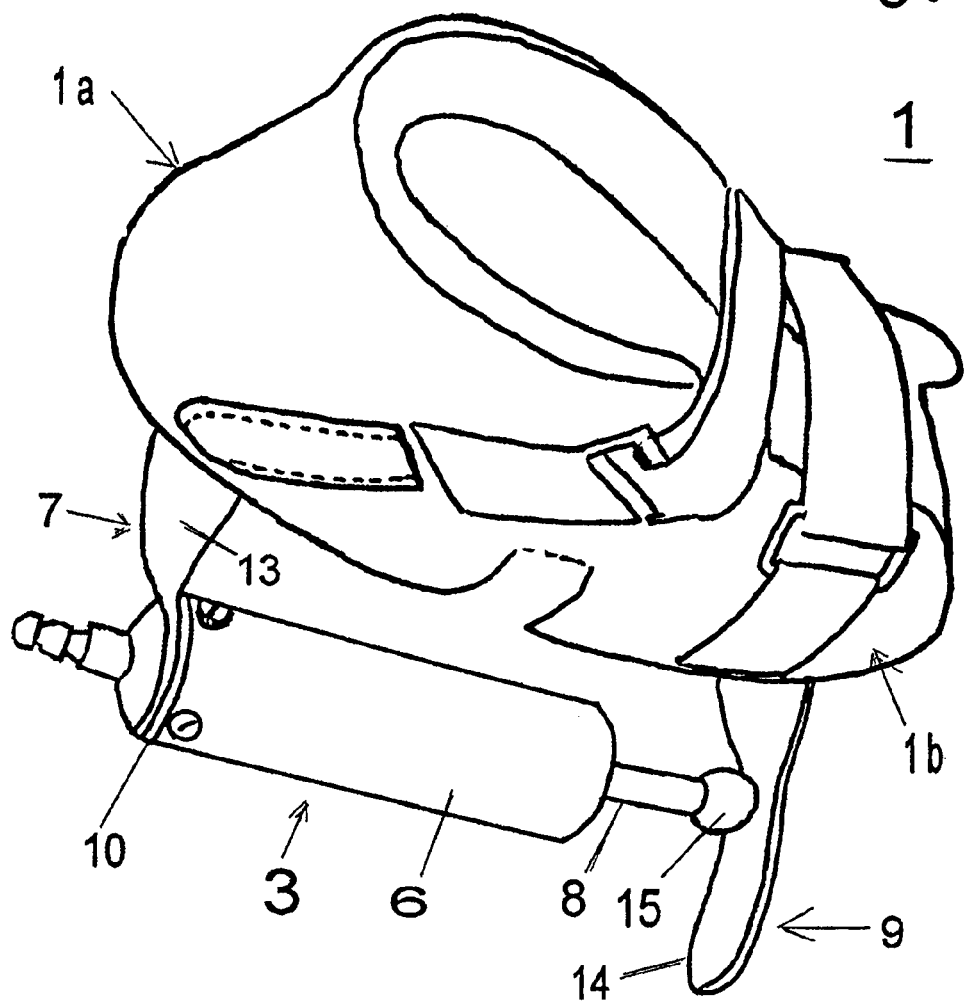
FIG. 3 is a perspective view of a Quengle cast designed as a pes adductus cast.
Figure 4:
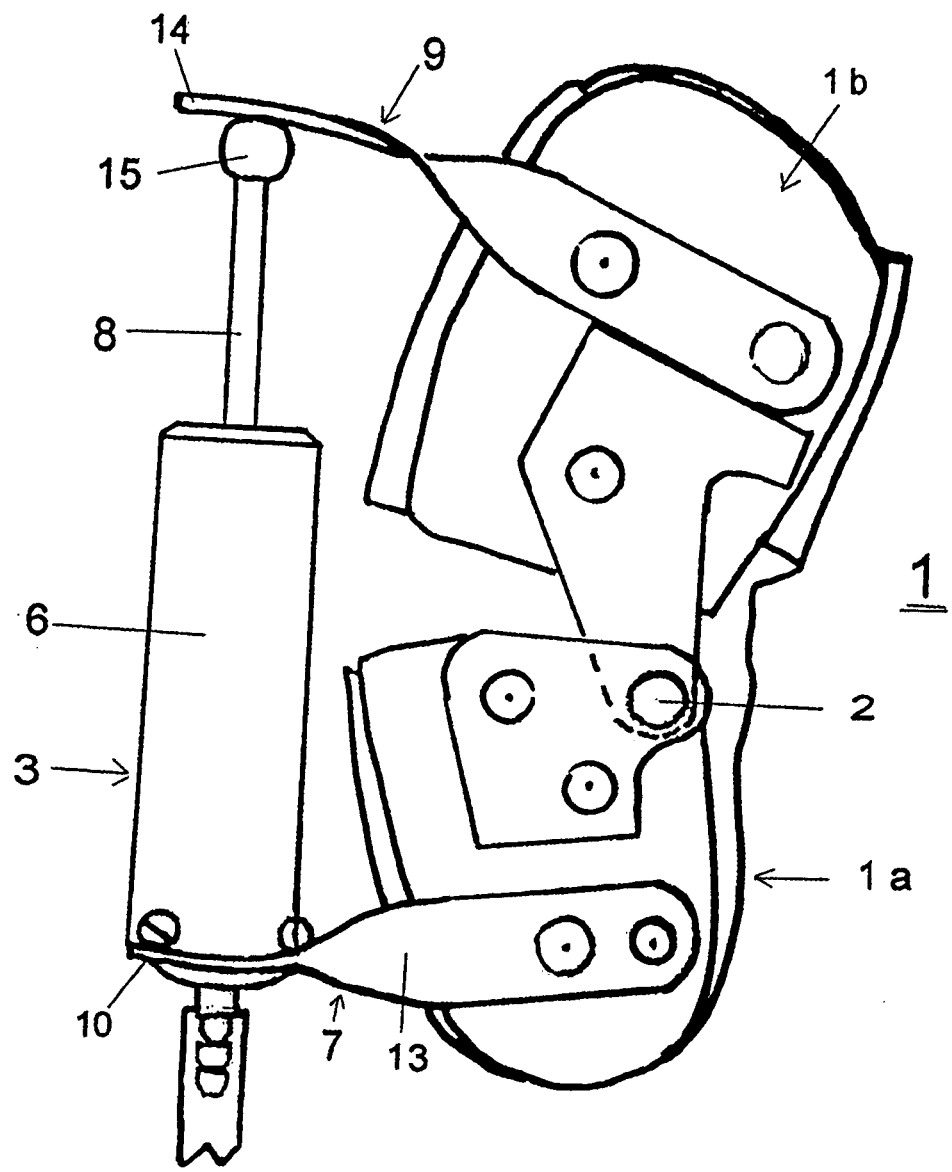
FIG. 4 s a top view of the underside of the pes adductus cast according to FIG. 3.

FIGS. 3 and 4 show a second exemplary embodiment of the Quengle cast 1 according to the present invention. The Quengle cast 1 is designed as a pes adductus cast in this case and is used to correct false positions of human feet.

Analogously to the exemplary embodiment according to FIGS. 1 and 2, the pes adductus cast likewise has two cast parts 1a and 1b, which are connected to each other in an articulated manner. The Quengle force is likewise preset via the pneumatic correcting unit 3, which is actuated by the control unit 5, not shown in FIGS. 3 and 4. Since the path of deflection is short in this case, which is typical of this cast, it is possible to do without a corresponding adjustment.

In the exemplary embodiments shown in FIGS. 1-4, the pneumatic correcting unit 3 has a hollow cylinder 6 as the basic body, which is fastened to the first cast part 1a by means of a first bracket 7. Furthermore, the pneumatic correcting unit 3 has a piston rod 8 as the adjusting member, which is in functional connection with a second bracket 9 on the second cast part 1b.

The rear part of the piston rod 8 is mounted displaceably in the hollow cylinder 6 in the longitudinal direction of this hollow cylinder. The adjusting member is actuated, i.e., the piston rod 8 is deflected, by the admission of pressure into the hollow cylinder 6 in such a way that this pressure is controlled via the control unit 5. Due to the fixation of the hollow cylinder 6, on the one hand, and of the piston rod 8, on the other hand, over the joint, a defined correction position of the Quengle cast 1 is reached due to the deflection of the piston rod 8, and a Quengle force is thus exerted on the human joint being held in the Quengle cast 1.

The bracket 7 at the first Quengle cast part 1a has a holding ring 10, which surrounds the hollow cylinder 6 on its jacket surface. In the exemplary embodiment according to FIGS. 1 and 2, this holding ring 10 is mounted on a fastening and adjusting unit 11. The fastening and adjusting unit 11 is fastened to the first cast part a by means of fastening means 12, which are formed by screw connections in this case. The hollow cylinder 6 can be displaced for its fixation in its longitudinal direction at the first cast part 1a by means of the fastening and adjusting unit 11 and then fixed in a desired position with the holding ring 10.

The hollow cylinder 6 is fixed by means of a supporting arm 13 in the exemplary embodiment according to FIGS. 3 and 4. The supporting arm 13 is fastened to the first cast part 1a and projects laterally from same.

The bracket 9 at the second cast part 1b is formed by a second supporting arm 14. The supporting arm 14 projects from the second cast part 1b in such a way that a segment of this supporting arm 14 forms an abutment, against which the front end of the piston rod 8 is pressed. As is apparent from FIGS. 1-4, the piston rod 8 has at its front end a spherical pressing element 15, which is in contact with the abutment of the supporting arm 14.

In the exemplary embodiment according to FIGS. 1 and 2, the supporting arm 14 at the second cast part 1b has an arc-shaped design, and the front end of the supporting arm 14 forms the abutment. The supporting arm 14 extends essentially linearly in the exemplary embodiment according to FIGS. 3 and 4. The front end of the supporting arm 14 forms the abutment in this case as well.

Figure 5:
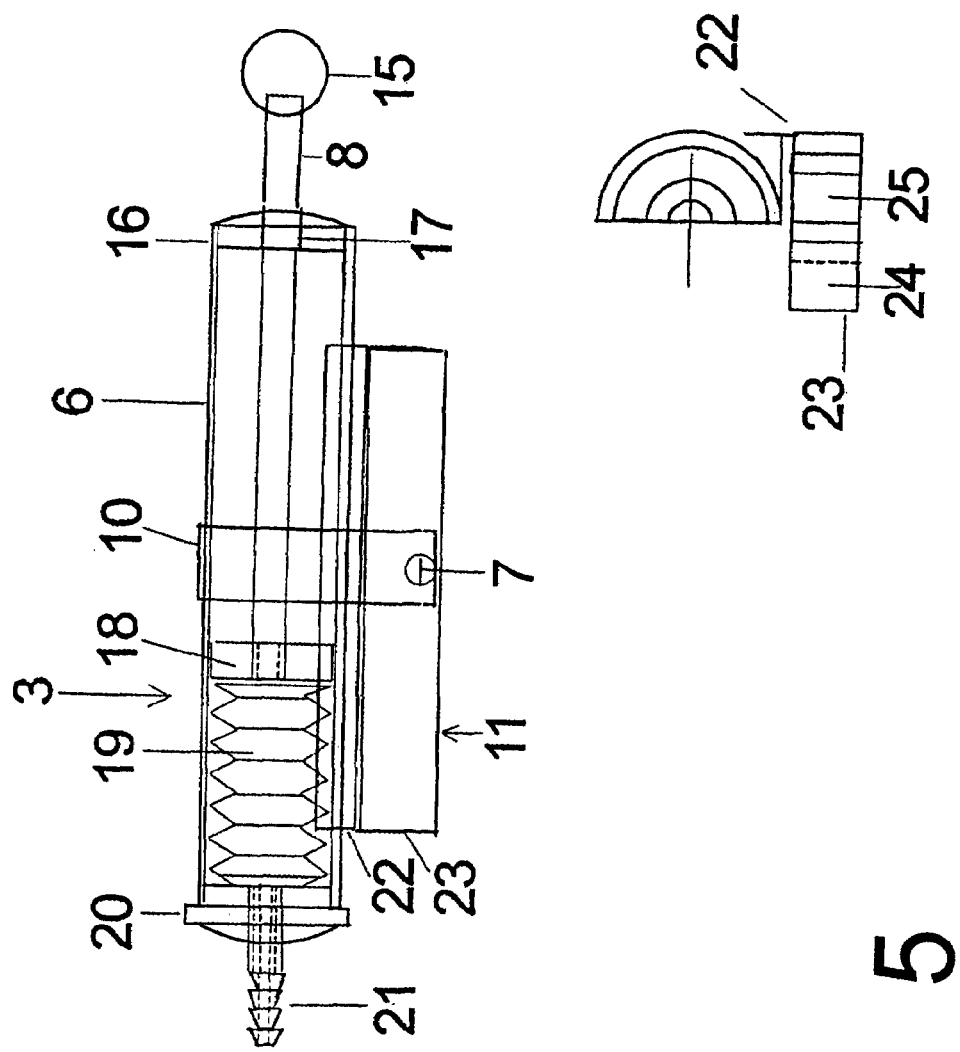
FIG. 5 is a longitudinal section and a cross-sectional view of a pneumatic correcting unit with a fastening and adjusting unit for a Quengle cast according to FIGS. 1 and 2.

The design of the pneumatic correcting unit 3 with the fastening and adjusting unit 11 according to the exemplary embodiment shown in FIGS. 1 and 2 is shown in detail in FIG. 5.

As is apparent from FIG. 5, the rear end of the piston rod 8 is guided in the hollow cylinder 6 of the pneumatic correcting unit 3, while the front end with the spherical pressing element 15 projects over the front end of the hollow cylinder 6. The hollow cylinder 6 preferably consists of an aluminum tube or a carbon fiber-reinforced plastic.

The piston rod 8 is located in the axis of symmetry of the hollow cylinder 6 and is mounted displaceably in the longitudinal direction of the hollow cylinder 6. A closing head 16, which ends at the hollow cylinder 6 at its front face, is provided for mounting the piston rod 8. A guide hole 17, in which the piston rod 8 is mounted, is provided in the closing head 16.

A circular disk-shaped piston 18, whose external diameter corresponds to the internal diameter of the hollow cylinder 6, is arranged at the rear end of the piston rod 8. A bellows 19 is connected on the rear side of the piston 18. The rear end of the bellows 19 is fastened to another closing head 20, which closes the hollow cylinder 6 on its rear face. A compressed air connection, which is formed by an air nozzle 21, opens into the closing head 20.

The piston 18 and the piston rod 8 consist of aluminum or stainless steel. The pressing element 15 preferably consists of polyamide. The closing heads 16, 20 preferably consist of aluminum and are screwed onto, screwed into or cast into the hollow cylinder 6. The air nozzle 21 preferably has a threaded section for insertion into a corresponding opening in the closing head 20 and for the airtight fixation of the bellows 19 with a round nut.

The bellows 19 is rotationally symmetrical to the axis of symmetry of the hollow cylinder 6 and preferably consists of a highly elastic, textile-reinforced material, especially latex. The external diameter of the bellows 19 is slightly smaller than the internal diameter of the hollow cylinder 6, so that the outer wall of the bellows 19 is movable along the wall of the hollow cylinder 6 with a small clearance.

Compressed air is introduced into the bellows 19 via the compressed air connection, as a result of which the bellows 19 expands in the longitudinal direction, and a preset force is exerted on the piston 18. This causes a defined deflection of the piston rod 8 and consequently a defined Quengle force.

By presetting the pressure in the bellows 19, which preferably varies within a range between 0.4 cm/Hg and 250 cm/Hg, a precise adjustment of the deflection of the piston rod 8 and thus a precise and reproducible presetting of the Quengle force are guaranteed. The maximum deflection of the piston rod 8 is preferably determined by means of an end switch, not shown.

Figure 6:
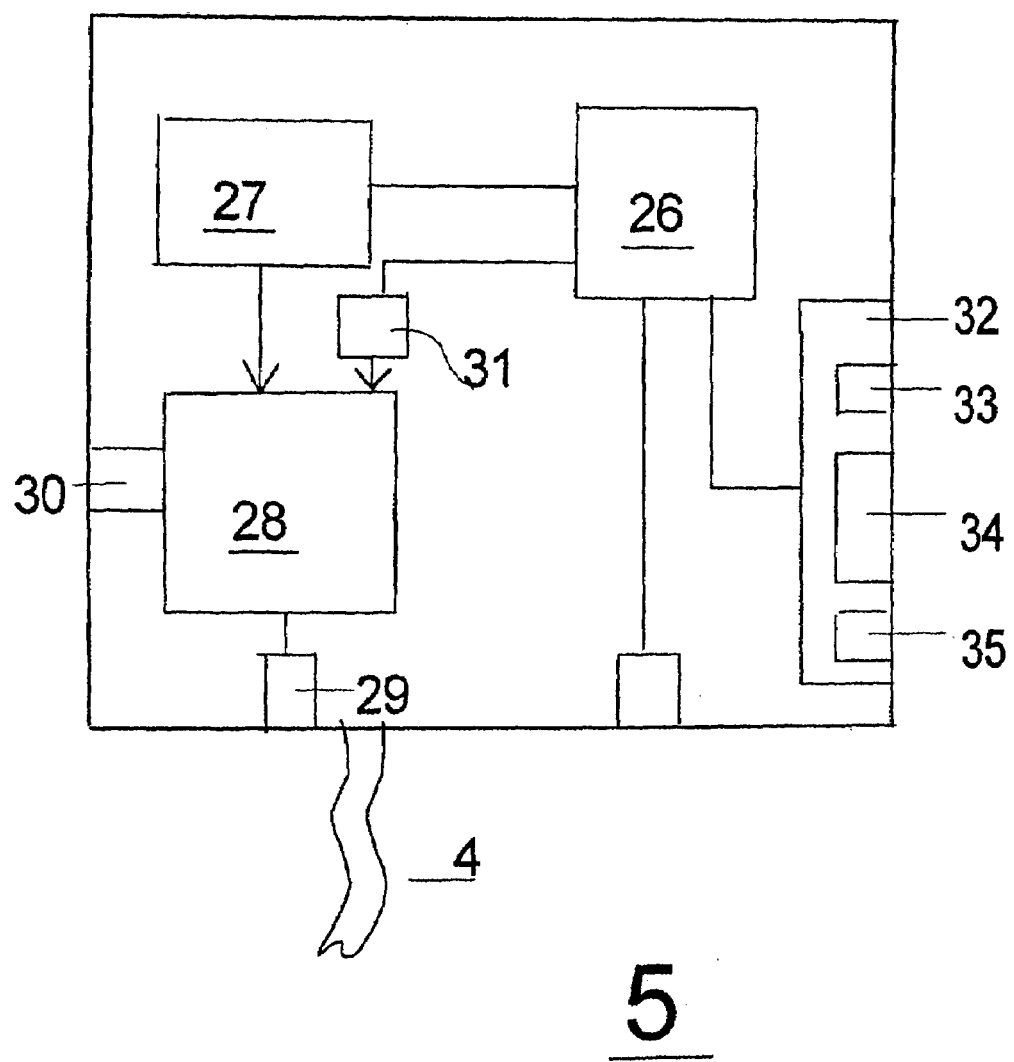
FIG. 6 provides detail views of components of the fastening and adjusting unit according to FIG. 5.

The pneumatic correcting unit 3 can be fastened by means of the fastening and adjusting unit 11 shown in FIGS. 5 and 6 to each Quengle cast 1 in such a way that its position can be adjusted. The fastening and adjusting unit 11 has two rails 22, 23, which extend in the longitudinal direction and lie one on top of another. The holding ring 10, which surrounds the jacket surface of the hollow cylinder 6 for the fixation of the pneumatic correcting unit 3, is fastened to the lower rail 23. The lower rail 23 is fastened, especially screwed, to the particular cast part 1a.

On their contact surfaces adjoining each other, the rails 22, 23 have toothed strips 24, 25 engaging each other. As is apparent from FIG. 5, the toothed strips 24, 25 of the rails 22, 23 have toothed segments arranged one after another in the longitudinal direction of the rails 22, 23. The toothed segments have identical square cross sections, which are constant over the entire width of the respective rails 22, 23. To set a desired position of the pneumatic correcting unit 3 at the respective cast part 1a, 1b, the toothed strips 24, 25 are brought into a corresponding relative position in relation to each other and then fixed against each other with the holding ring 10.

Figure 7:
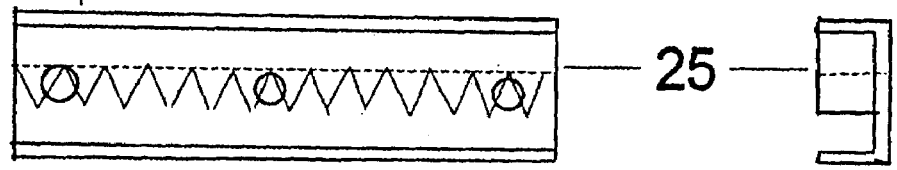
FIG. 7 is a block diagram of a control unit for a Quengle cast according to FIGS. 1-4.
Figure 7:
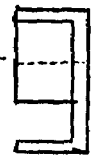
Figure 7:
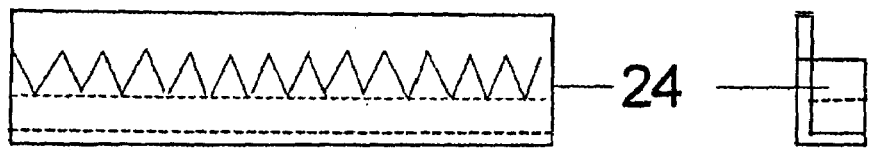
Figure 7:
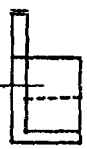
Figure 7:
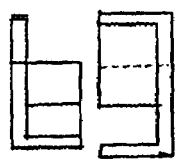

As is apparent from FIG. 7, the first rail 22 is designed as an angle rail, while the second rail 23 is designed as a U rail. The toothed segments are screwed in the rails 22, 23 at right angles to the width of the rails flush with the respective angle. The rail 22 is fastened to the hollow cylinder. For adjustment in the longitudinal direction, the rail 22 with the toothed segments is lifted off from the rail 23, displaced by the necessary length and again inserted with the toothed segments into the toothed segments of the rail 23. The holding ring 10 fixes the rail 22 with the hollow cylinder 6 against the rail 23, which is fastened to the Quengle cast 1.

FIG. 6 shows a block diagram of the control unit 5, by means of which the pneumatic correcting unit 3 is controlled. The control unit 5 is integrated in a housing and has a computer unit 26, which is formed by a microcontroller or a microprocessor. Furthermore, the control unit 5 has a pump 27, an air reservoir 28 and a compressed air connection 29. The pump 27 is connected to the computer unit 26 and is controlled by same.

Via the pump 27, compressed air is fed into the pneumatic correcting unit 3 through the air reservoir 28 via the flexible tube 4 connected to the compressed air connection 29. The volume of the air reservoir 28 is considerably larger than the volume of the bellows 19. The volume of the air reservoir 28 is preferably about 250 cc. It is guaranteed as a result that the air pressure in the bellows 19 can be rapidly and precisely adjusted to a set point preset via the computer unit 26 by means of the control unit 5, as a result of which a continuous displacing movement of the piston rod 8 is achieved.

To reduce the pressure in the air reservoir 28, a release valve 30 is provided, which can be actuated manually or via the computer unit 26.

The air pressure in the bellows 19 of the pneumatic correcting unit 3 and consequently the Quengle force generated are controlled via the computer unit 26 by the suitable actuation of the pump 27. Pressure regulation is preferably performed via the computer unit 26, the air pressure in the air reservoir 28 being monitored by means of a pressure control device 31.

Furthermore, an input/output unit 32 is connected to the computer unit 26. This has a switch 33 for switching the control unit 5 on and off. In addition, an operating interface 34 is provided for entering parameter values in the computer unit 26. In particular, it is possible as a result to set the set points, to which the air pressure is to be regulated by means of the computer unit 26, and the ranges within which the air pressure may vary. In addition, the measured values generated and stored in the computer unit 26, especially pressure values as well as utilization or use times, can be outputted via the operating interface 34, so that these can be checked during the entire operation of the control unit 5. Complete and comprehensive therapy control is guaranteed as a result.

The operating interface 34 of the input/output unit 32 has, in particular, a connection for a printer, by means of which the measured values can be recorded over a predetermined period of time. Moreover, the operating interface 34 of the input/output unit 32 has a digital display for displaying the current measured values. Finally, the operating interface 34 of the input/output unit 32 has an operating part for entering parameter values.

The control unit 5 has, furthermore, an electric connection, to which the end switch in the pneumatic correcting unit 3 can be connected via a cable connection. As a result, it is possible to monitor in the computer unit 26 whether the end position of the piston rod 8 has been reached. The fact that the end position is reached is displayed via the input/output unit 32. This preferably has a light-emitting diode 35 for this purpose.

Finally, the control unit 5 has a power supply unit, not shown, especially a battery. The control unit 5 is arranged especially advantageously in a compact housing, not shown, so that the control unit forms a portable and consequently mobile unit with the Quengle cast 1 and the pneumatic control unit 3.

While specific embodiments of the invention have been shown and described in detail to illustrate the application of the principles of the invention, it will be understood that the invention may be embodied otherwise without departing from such principles.

LIST OF REFERENCE NUMBERS

| | |
|---|---|
| (1) | Quengle cast |
| (1a) | First cast part |
| (1b) | Second cast part |
| (2) | Articulated connection |
| (3) | Pneumatic correcting unit |
| (4) | Flexible tube |
| (5) | Control unit |
| (6) | Hollow cylinder |
| (7) | First bracket |
| (8) | Piston rod |
| (9) | Second bracket |
| (10) | Holding ring |
| (11) | Fastening and adjusting unit |
| (12) | Fastening means |
| (13) | First supporting arm |
| (14) | Second supporting arm |
| (15) | Pressing element |
| (16) | Closing head |
| (17) | Guide hole |
| (18) | Piston |
| (19) | Bellows |
| (20) | Closing head |
| (21) | Air nozzle |
| (22) | Rail |
| (23) | Rail |
| (24) | Toothed strip |
| (25) | Toothed strip |
| (26) | Computer unit |
| (27) | Pump |
| (28) | Air reservoir |
| (29) | Compressed air connection |
| (30) | Release valve |
| (31) | Pressure control device |
| (32) | Input/output unit |
| (33) | Switch |
| (34) | Operating interface |
| (35) | Light-emitting diode |

The invention claimed is:

1. A corrective orthesis for the correction of false positions of a joint, the orthesis comprising:
 a correcting unit with a pressurized basic body and an adjusting member for generating a Quengle/corrective force acting on the joint;
 a control unit selectively applying a pressure in the basic body to generate a defined Quengle force, as a result of which the adjusting member is deflectable in relation to the basic body, said correcting unit being designed as a pneumatic correcting unit which has a hollow cylinder as said basic body and a piston rod mounted displaceably in said hollow cylinder as the adjusting member, wherein a force and path of displacement of said piston rod can be preset by selecting an air pressure in said hollow cylinder, wherein a piston is arranged at a rear end of said piston rod which protrudes into said hollow cylinder, said piston having a diameter corresponding to an internal diameter of said hollow cylinder, wherein a bellows is connected to a rear side of said piston such that compressed air can be admitted into said bellows.

2. The corrective orthesis in accordance with claim 1, wherein:
 a closing head with a guide hole is provided on a front face of said hollow cylinder, said piston rod being mounted displaceably in a longitudinal direction of said hollow cylinder in said guide hole.

3. The corrective orthesis in accordance with claim 2, wherein said correcting unit and said control unit form a portable unit.

4. The corrective orthesis in accordance with claim 1, wherein: two cast parts are connected to each other in an articulated manner, a first cast part has a bracket for fastening to a basic body, and a second cast part has a bracket that is in functional connection with the adjusting member, so that said cast parts can be pivoted in relation to each other when the adjusting member is actuated.

5. The corrective orthesis in accordance with claim 4, wherein: said piston rod has at a front end a spherical pressing element which is in contact with a segment of said bracket, said segment forming an abutment.

6. The corrective orthesis in accordance with claim 4, wherein: said hollow cylinder forms the basic body for fixation at said first cast part and is surrounded on a jacket surface by a holding ring.

7. The corrective orthesis in accordance with claim 6, wherein: said holding ring is part of a supporting arm which projects from said first cast part and forms said bracket.

8. The corrective orthesis in accordance with claim 7, wherein: said holding ring is part of a fastening and adjusting unit which forms said bracket, and said bracket adjustably fastens said hollow cylinder to said first cast part.

9. The corrective orthesis in accordance with claim 8, wherein: said fastening and adjusting unit has two rails which are located one inside the other and extend in the longitudinal direction of said hollow cylinder, said rails have toothed strips engaging each other in a positive-locking manner on their angle surfaces engaging each other.

10. The corrective orthesis in accordance with claim 9, wherein: said rails can be fixed in adjustable relative positions by means of said holding ring.

11. The corrective orthesis in accordance with claim 9, wherein: a first of said rails is fastened to said hollow cylinder, a second of said rails is fastened to said first cast part by a fastener.

12. The corrective orthesis in accordance with claim 1, wherein: said control unit has an air reservoir, a pump and a compressed air connection, wherein compressed air can be fed to the correcting unit by said pump through said air reservoir via said compressed air connection.

13. The corrective orthesis in accordance with claim 12, wherein: compressed air connections are connected at said control unit and at said hollow cylinder via a flexible tube.

14. The corrective orthesis in accordance with claim 12, wherein a volume of said air reservoir is considerably larger than a volume of said hollow cylinder.

15. The corrective orthesis in accordance with claim 12, wherein: said control unit has a computer unit for presetting pressure in said correcting unit.

16. The corrective orthesis in accordance with claim 15, wherein: said pump is actuated by said computer unit.

17. The corrective orthesis in accordance with claim 15, wherein: pressure regulation is performed by said computer unit.

18. The corrective orthesis in accordance with claim 15, wherein: an input/output unit is associated with said computer unit.

19. The corrective orthesis in accordance with claim 18, wherein: set points for setting pressure can be preset via said input/output unit.

20. The corrective orthesis in accordance with claim 19, wherein: utilization data, especially date and operating time, which are generated and stored in said computer unit can be outputted via said input/output unit.

21. The corrective orthesis in accordance with claim 19, wherein: a pressure control device for controlling a set pressure in said air reservoir is connected to said computer unit, wherein measured values generated by said pressure control device can be outputted via said input/output unit.

22. The corrective orthesis in accordance with claim 19, wherein: an end switch is arranged in the computer unit and is connected to said computer unit, said end switch for detecting an end position of said piston rod, said input/output unit displays a signal that the end position is reached.

23. The corrective orthesis in accordance with claim 1, wherein: said correcting unit and said control unit forms a portable unit.

24. A corrective orthesis for the correction of false positions of a joint, the orthesis comprising:
 a correcting unit with a pressurized basic body and an adjusting member for generating a Quengle/corrective force acting on the joint;
 a control unit selectively applying a pressure in the basic body to generate a defined Quengle force, as a result of which the adjusting member is deflectable in relation to the basic body, said correcting unit being designed as a pneumatic correcting unit which has a hollow cylinder as said basic body and a piston rod mounted displaceably in said hollow cylinder as the adjusting member, wherein a force and path of displacement of said piston rod can be preset by selecting an air pressure in said hollow cylinder, wherein a piston is arranged at a rear end of said piston rod which protrudes into said hollow cylinder, said piston having a diameter corresponding to an internal diameter of said hollow cylinder, wherein a bellows is connected to a rear side of said piston such that compressed air can be admitted into said bellows, wherein a rear end of said bellows joins a closing head on a rear face of said hollow cylinder, wherein a compressed air connection is arranged in said closing head for feeding compressed air into said bellows.

25. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body, said correcting unit being designed as a pneumatic correcting unit which has a hollow cylinder as said basic body and a piston rod mounted displaceably in said hollow cylinder as the adjusting member, wherein a force and path of displacement of said piston rod can be preset by selecting an air pressure in said hollow cylinder, wherein a piston is arranged at a rear end of said piston rod which protrudes into said hollow cylinder, said piston having a diameter corresponding to an internal diameter of said hollow cylinder, wherein a bellows is connected to a rear side of said piston such that compressed air can be admitted into said bellows, wherein a rear end of said bellows joins a closing head on a rear face of said hollow cylinder, wherein a compressed air connection is arranged in said closing head for feeding compressed air into said bellows, said compressed air connection being formed by an air nozzle.

26. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body, said correcting unit being designed as a pneumatic correcting unit which has a hollow cylinder as said basic body and a piston rod mounted displaceably in said hollow cylinder as the adjusting member, wherein a force and path of displacement of said piston rod can be preset by selecting an air pressure in said hollow cylinder, wherein a piston is arranged at a rear end of said piston rod which protrudes into said hollow cylinder, said piston having a diameter corresponding to an internal diameter of said hollow cylinder, wherein a bellows is connected to a rear side of said piston such that compressed air can be admitted into said bellows, said bellows including an elastic, textile-reinforced material.

27. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body, said correcting unit being designed as a pneumatic correcting unit which has a hollow cylinder as said basic body and a piston rod mounted displaceably in said hollow cylinder as the adjusting member, wherein a force and path of displacement of said piston rod can be preset by selecting an air pressure in said hollow cylinder, wherein a piston is arranged at a rear end of said piston rod which protrudes into said hollow cylinder, said piston having a diameter corresponding to an internal diameter of said hollow cylinder, wherein a bellows is connected to a rear side of said piston such that compressed air can be admitted into said bellows, said bellows being symmetrical to a longitudinal axis of said hollow cylinder, wherein an external diameter of said bellows is adapted to the internal diameter of said hollow cylinder.

28. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body;

a first cast part;

a second cast part, said first cast part being connected to said first cast part in an articulated manner, said first cast part having a first bracket for fastening to the basic body, said second cast part having a second bracket that is in functional connection with the adjusting member such that said first cast part pivots relative to said second cast part when the adjusting member is actuated;

a piston rod having at a front end a spherical pressing element, said spherical pressing element being in contact with a segment of said second bracket, said segment forming an abutment.

29. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body;

a first cast part;

a second cast part, said first cast part being connected to said first cast part in an articulated manner, said first cast part having a first bracket for fastening to the basic body, said second cast part having a second bracket that is in functional connection with the adjusting member such that said first cast part pivots relative to said second cast part when the adjusting member is actuated, wherein a hollow cylinder forms the basic body for fixation at said first cast part and is surrounded on a jacket surface by a holding ring.

30. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body;

a first cast part;

a second cast part, said first cast part being connected to said first cast part in an articulated manner, said first cast part having a first bracket for fastening to the basic body, said second cast part having a second bracket that is in functional connection with the adjusting member such that said first cast part pivots relative to said second cast part when the adjusting member is actuated, wherein a hollow cylinder forms the basic body for fixation at said first cast part and is surrounded on a jacket surface by a holding ring, said holding ring being part of a supporting arm which projects from said first cast part and forms said first bracket.

31. A corrective orthesis for the correction of false positions of a joint, the orthesis comprising:
- a correcting unit with a pressurized basic body and an adjusting member for generating a Quengle/corrective force acting on the joint;
- a control unit selectively applying a pressure in the basic body to generate a defined Quengle force, as a result of which the adjusting member is deflectable in relation to the basic body;
- a first cast part;
- a second cast part, said first cast part being connected to said first cast part in an articulated manner, said first cast part having a first bracket for fastening to the basic body, said second cast part having a second bracket that is in functional connection with the adjusting member such that said first cast part pivots relative to said second cast part when the adjusting member is actuated, wherein a hollow cylinder forms the basic body for fixation at said first cast part and is surrounded on a jacket surface by a holding ring, said holding ring being part of a supporting arm which projects from said first cast part and forms said first bracket, said holding ring being a part of a fastening and adjusting unit which forms said first bracket, said bracket adjustably fastening said hollow cylinder to said first cast part.

32. A corrective orthesis for the correction of false positions of a joint, the orthesis comprising:
- a correcting unit with a pressurized basic body and an adjusting member for generating a Quengle/corrective force acting on the joint;
- a control unit selectively applying a pressure in the basic body to generate a defined Quengle force, as a result of which the adjusting member is deflectable in relation to the basic body;
- a first cast part;
- a second cast part, said first cast part being connected to said first cast part in an articulated manner, said first cast part having a first bracket for fastening to the basic body, said second cast part having a second bracket that is in functional connection with the adjusting member such that said first cast part pivots relative to said second cast part when the adjusting member is actuated, wherein a hollow cylinder forms the basic body for fixation at said first cast part and is surrounded on a jacket surface by a holding ring, said holding ring being part of a supporting arm which projects from said first cast part and forms said first bracket, said holding ring being a part of a fastening and adjusting unit which forms said first bracket, said bracket adjustably fastening said hollow cylinder to said first cast part, said fastening and adjusting unit having two rails located one inside the other, said rails extending in the longitudinal direction of said hollow cylinder, said rails having toothed strips engaging each other in a positive-locking manner on their angle surfaces engaging each other.

33. A corrective orthesis for the correction of false positions of a joint, the orthesis comprising:
- a correcting unit with a pressurized basic body and an adjusting member for generating a Quengle/corrective force acting on the joint;
- a control unit selectively applying a pressure in the basic body to generate a defined Quengle force, as a result of which the adjusting member is deflectable in relation to the basic body;
- a first cast part;
- a second cast part, said first cast part being connected to said first cast part in an articulated manner, said first cast part having a first bracket for fastening to the basic body, said second cast part having a second bracket that is in functional connection with the adjusting member such that said first cast part pivots relative to said second cast part when the adjusting member is actuated, wherein a hollow cylinder forms the basic body for fixation at said first cast part and is surrounded on a jacket surface by a holding ring, said holding ring being part of a supporting arm which projects from said first cast part and forms said first bracket, said holding ring being a part of a fastening and adjusting unit which forms said first bracket, said bracket adjustably fastening said hollow cylinder to said first cast part, said fastening and adjusting unit having two rails located one inside the other, said rails extending in the longitudinal direction of said hollow cylinder, said rails having toothed strips engaging each other in a positive-locking manner on their angle surfaces engaging each other, said rails being fixed in adjustable relative positions via said holding ring.

34. A corrective orthesis for the correction of false positions of a joint, the orthesis comprising:
- a correcting unit with a pressurized basic body and an adjusting member for generating a Quengle/corrective force acting on the joint;
- a control unit selectively applying a pressure in the basic body to generate a defined Quengle force, as a result of which the adjusting member is deflectable in relation to the basic body;
- a first cast part;
- a second cast part, said first cast part being connected to said first cast part in an articulated manner, said first cast part having a first bracket for fastening to the basic body, said second cast part having a second bracket that is in functional connection with the adjusting member such that said first cast part pivots relative to said second cast part when the adjusting member is actuated, wherein a hollow cylinder forms the basic body for fixation at said first cast part and is surrounded on a jacket surface by a holding ring, said holding ring being part of a supporting arm which projects from said first cast part and forms said first bracket, said holding ring being a part of a fastening and adjusting unit which forms said first bracket, said bracket adjustably fastening said hollow cylinder to said first cast part, said fastening and adjusting unit having two rails located one inside the other, said rails extending in the longitudinal direction of said hollow cylinder, said rails having toothed strips engaging each other in a positive-locking manner on their angle surfaces engaging each other, one of said rails being fastened to said hollow cylinder, another of said rails being fastened to said first cast part via a fastener.

35. A corrective orthesis for the correction of false positions of a joint, the orthesis comprising:
- a correcting unit with a pressurized basic body and an adjusting member for generating a Quengle/corrective force acting on the joint;
- a control unit selectively applying a pressure in the basic body to generate a defined Quengle force, as a result of which the adjusting member is deflectable in relation to the basic body, said control unit having an air reservoir, a pump and a compressed air connection, wherein compressed air can be fed to the correcting unit by said pump through said air reservoir via said compressed air connection.

36. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body, wherein compressed air connections are connected at said control unit and at a hollow cylinder via a flexible tube, said control unit having an air reservoir, a pump and a compressed air connection, wherein compressed air is fed to the correcting unit by said pump through said air reservoir via said compressed air connection.

37. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body, said control unit having an air reservoir, a pump and a compressed air connection, wherein compressed air can be fed to the correcting unit by said pump through said air reservoir via said compressed air connection, said air reservoir having a volume larger than a volume of a hollow cylinder.

38. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body, said control unit having an air reservoir, a pump and a compressed air connection, wherein compressed air can be fed to the correcting unit by said pump through said air reservoir via said compressed air connection, said control unit having a computer unit for presetting pressure in said correcting unit.

39. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body, said control unit having an air reservoir, a pump and a compressed air connection, wherein compressed air can be fed to the correcting unit by said pump through said air reservoir via said compressed air connection, said control unit having a computer unit for presetting pressure in said correcting unit, said pump being actuated via said computer unit.

40. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body, said control unit having an air reservoir, a pump and a compressed air connection, wherein compressed air can be fed to the correcting unit by said pump through said air reservoir via said compressed air connection, said control unit having a computer unit for presetting pressure in said correcting unit, said computer unit regulating pressure in said pressurized basic body.

41. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body, said control unit having an air reservoir, a pump and a compressed air connection, wherein compressed air can be fed to the correcting unit by said pump through said air reservoir via said compressed air connection, said control unit having a computer unit for presetting pressure in said correcting unit, wherein an input/output unit is associated with said computer unit.

42. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body, said control unit having an air reservoir, a pump and a compressed air connection, wherein compressed air can be fed to the correcting unit by said pump through said air reservoir via said compressed air connection, said control unit having a computer unit for presetting pressure in said correcting unit, wherein an input/output unit is associated with said computer unit, said input/output unit setting points for setting pressure.

43. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body, said control unit having an air reservoir, a pump and a compressed air connection, wherein compressed air can be fed to the correcting unit by said pump through said air reservoir via said compressed air connection, said control unit having a computer unit for presetting pressure in said correcting unit, wherein an input/output unit is associated with said computer unit, said input/output unit setting points for setting pressure, said input/output unit providing utilization data as output.

44. A corrective orthesis for the correction of false positions of a joint, the orthesis comprising:

a correcting unit with a pressurized basic body and an adjusting member for generating a Quengle/corrective force acting on the joint;

a control unit selectively applying a pressure in the basic body to generate a defined Quengle force, as a result of which the adjusting member is deflectable in relation to the basic body, said control unit having an air reservoir, a pump and a compressed air connection, wherein compressed air can be fed to the correcting unit by said pump through said air reservoir via said compressed air connection, said control unit having a computer unit for presetting pressure in said correcting unit, wherein an input/output unit is associated with said computer unit, said input/output unit setting points for setting pressure, said computer unit being connected to a pressure control device, said pressure control device controlling a set pressure in said air reservoir, said input/output unit providing as output measured values generated by said pressure control device.

45. A corrective orthesis for the correction of false positions of a joint, the orthesis comprising:
- a correcting unit with a pressurized basic body and an adjusting member for generating a Quengle/corrective force acting on the joint;
- a control unit selectively applying a pressure in the basic body to generate a defined Quengle force, as a result of which the adjusting member is deflectable in relation to the basic body, said control unit having an air reservoir, a pump and a compressed air connection, wherein compressed air can be fed to the correcting unit by said pump through said air reservoir via said compressed air connection, said control unit having a computer unit for presetting pressure in said correcting unit, wherein an input/output unit is associated with said computer unit, said input/output unit setting points for setting pressure, said computer unit having an end switch arranged therein, said end switch being connected to said computer unit, said end switch detecting an end position of a piston rod, said input/output unit displaying a signal when said end position has been reached.

* * * * *